United States Patent
Leynov et al.

(10) Patent No.: US 8,506,615 B2
(45) Date of Patent: Aug. 13, 2013

(54) IMPLANTABLE MEDICAL ENDOPROSTHESIS DELIVERY SYSTEM

(75) Inventors: Alexander Leynov, Walnut Creek, CA (US); Robert Obara, Fremont, CA (US); Masoud Molaei, Mountain View, CA (US); Hong Doan, Santa Clara, CA (US); Lukas Roush, Pleasanton, CA (US); Jennifer M. Arends, San Carlos, CA (US); John Peckham, Mountain View, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 0 days.

(21) Appl. No.: 13/345,369

(22) Filed: Jan. 6, 2012

(65) Prior Publication Data

US 2012/0116494 A1    May 10, 2012

Related U.S. Application Data

(63) Continuation of application No. 11/395,479, filed on Mar. 30, 2006, now Pat. No. 8,092,508.

(51) Int. Cl.
*A61F 2/06* (2006.01)
*A61B 17/00* (2006.01)

(52) U.S. Cl.
USPC .......... 623/1.11; 606/108; 606/190; 606/191; 606/194; 606/195; 606/198

(58) Field of Classification Search
USPC .............. 623/1.11, 1.12; 606/108, 191, 194, 606/195, 198; 604/96.01; 600/585
See application file for complete search history.

(56) References Cited

U.S. PATENT DOCUMENTS

| | | | |
|---|---|---|---|
| 5,026,377 A | 6/1991 | Burton et al. | |
| 5,437,288 A | 8/1995 | Schwartz et al. | |
| 5,534,077 A | 7/1996 | Litchblau et al. | |
| 5,645,559 A | 7/1997 | Hachtman et al. | |
| 5,741,429 A | 4/1998 | Donadio, III et al. | |
| 5,772,669 A | 6/1998 | Vrba | |
| 5,833,632 A | 11/1998 | Jacobsen et al. | |
| 6,042,589 A * | 3/2000 | Marianne | 606/108 |
| 6,068,634 A * | 5/2000 | Lorentzen Cornelius et al. | 623/1.11 |
| 6,120,522 A | 9/2000 | Vrba et al. | |
| 6,231,598 B1 | 5/2001 | Berry et al. | |
| 6,315,790 B1 | 11/2001 | Gerberding et al. | |
| 6,342,066 B1 | 1/2002 | Toro et al. | |

(Continued)

FOREIGN PATENT DOCUMENTS

| | | |
|---|---|---|
| WO | 9748343 A | 12/1997 |
| WO | 9922651 A | 5/1999 |
| WO | 9947075 A | 9/1999 |
| WO | 02056798 A | 7/2002 |

OTHER PUBLICATIONS

International Search Report mailed Sep. 18, 2007, in related International Application No. PCT/US2007/065327, filed Mar. 28, 2007.

(Continued)

*Primary Examiner* — Vy Q Bui
(74) *Attorney, Agent, or Firm* — Vista IP Law Group LLP (57) ABSTRACT

Implantable medical endoprosthesis delivery systems and articles are provided.

6 Claims, 11 Drawing Sheets

(56) References Cited

U.S. PATENT DOCUMENTS

| | | |
|---|---|---|
| 6,425,898 B1 | 7/2002 | Wilson et al. |
| 6,428,489 B1 | 8/2002 | Jacobsen et al. |
| 6,592,592 B1 | 7/2003 | Cox |
| 6,602,226 B1 | 8/2003 | Smith et al. |
| 6,620,191 B1 | 9/2003 | Svensson |
| 6,676,667 B2 | 1/2004 | Mareiro et al. |
| 6,743,219 B1 | 6/2004 | Dwyer et al. |
| 7,367,989 B2 | 5/2008 | Eidenschink |
| 2003/0109886 A1* | 6/2003 | Keegan et al. ............ 606/108 |
| 2006/0058865 A1 | 3/2006 | Case et al. |

OTHER PUBLICATIONS

Written Opinion mailed Sep. 18, 2007, in related International Application No. PCT/US2007/065327, filed Mar. 28, 2007.

Boston Scientific, "Neuroform microdelivery stent system," printed from www.bostonscientific.ie/med_specialty Apr. 4, 2005.

Boston Scientific, "Summary of safety and probable benefit," H020002, Sep. 11, 2002.

Medtronic, "Driver over-the-wire coronary stent system," printed from www.medtronic.com/medtronic_vascular/cs_driver.html Apr. 1, 2005.

Medtronic, "Racer over-the-wire biliary stent system," printed from www.medtronic.com/medtronic_vascular/ps_racer.html Apr. 1, 2005.

Medtronic, "S660 with discrete technology coronary stent system," printed from www.medtronic.com/medtronic_vascular/cs_s660.html Apr. 1, 2005.

* cited by examiner

IMPLANTABLE MEDICAL ENDOPROSTHESIS DELIVERY SYSTEM

RELATED APPLICATION DATA

The present application is a continuation of pending U.S. patent application Ser. No. 11/395,479, filed Mar. 30, 2006, the priority of which is hereby claimed under 35 USC. §120, and the contents of which is hereby incorporated herein by reference in its entirety, as though set forth in full.

TECHNICAL FIELD

This disclosure generally relates to implantable medical endoprosthesis delivery systems and related components, as well as related methods.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer member surrounding an inner member with a stent positioned therebetween. Generally, the operator of the system positions the distal portion within the lumen at a desired location (e.g., so that the stent is adjacent an occlusion). The operator can then retract the outer member to allow the stent to engage the occlusion/lumen wall. Thereafter, the operator removes the distal portion of the system from the lumen.

SUMMARY

In a first aspect, implantable medical endoprosthesis delivery systems are provided that include a delivery member, a sheath, and an endoprosthesis disposed between the delivery member and the sheath. A second member is included, the second member being configured so that when the sheath moves proximally or distally with respect to the delivery member, the endoprosthesis remains substantially stationary in a longitudinal direction with respect to the delivery member, and when the delivery member moves proximally or distally, the endoprosthesis remains substantially stationary with respect to the delivery member.

In a second aspect, implantable medical endoprosthesis delivery systems are provided that include a delivery member, a sheath, an endoprosthesis disposed between the delivery member and the sheath, and a seating member disposed between the delivery member and the endoprosthesis.

In another aspect, implantable medical endoprosthesis delivery systems are provided, the systems including a delivery member, a sheath, an endoprosthesis disposed between the delivery member and the sheath, and a coating supported by the delivery member and disposed between the delivery member and the endoprosthesis.

In still another aspect, implantable medical endoprosthesis delivery systems are provided, the systems including a delivery member, a sheath, an endoprosthesis disposed between the delivery member and the sheath, and windings of a material supported by the delivery member.

In yet another aspect, articles are provided, the articles including a first material having a first portion, a second portion, and a third portion disposed between the first and second portions, and windings of a second material supported by the first and second portions of the first material. The second material is unsupported by the third portion of the first material. The article can be, e.g., a delivery wire or a guide wire, which itself can be a delivery wire.

In another aspect, implantable medical endoprosthesis delivery systems are provided. The systems comprise a wire that includes a first material having a first portion, a second portion, and a third portion disposed between the first and second portions, and windings of a second material supported by the first and third portions of the first material. The systems further include a sheath and an endoprosthesis disposed between the wire and the sheath.

In a method aspect, methods are provided that include withdrawing a sheath to at least partially uncover an endoprosthesis that was previously disposed within the sheath, thereby allowing the at least a portion of the endoprosthesis to expand, and advancing the sheath to cover at least some of the expanded portion of the endoprosthesis, thereby disposing at least some of the expanded portion of the endoprosthesis within the sheath.

In another method aspect, methods are provided that include providing a system including an endoprosthesis in a sheath, the endoprosthesis having first and second portions. The sheath is withdrawn to expand the first portion of the endoprosthesis. The sheath is then advanced to cover the first portion of the endoprosthesis.

Embodiments can include one or more of the following features.

In some embodiments, the delivery member is a delivery wire, which can optionally function as a guidewire. In certain embodiments, the delivery member is a tube, e.g., a slotted hypotube, optionally having a guidewire lumen therein.

In some embodiments, the implantable medical endoprosthesis is a self-expanding endoprosthesis.

In some embodiments, the second member is disposed between the delivery member and the sheath. The second member can, for example, be disposed on (e.g., attached to) the delivery member, such that the second member forms a seating for the implantable medical endoprosthesis. The second member can comprise a resilient, soft, and/or tacky material against which the implantable medical endoprosthesis resides. The second member can comprise a material having a durometer of 55 D or less. The second member can include a plurality of members.

In some embodiments, the system can further include a proximal sub-bumper located proximal to the second member and attached to the delivery wire, and a distal sub-bumper located distal to the second member and attached to the delivery wire. The second member can have a lumen having a diameter larger than a diameter of the delivery member and through which the delivery member extends, the diameter of the lumen in the second member being smaller than a diameter of the proximal and distal sub-bumpers.

In some embodiments, the secondary member can include a coating (e.g., a polymer coating) supported by the delivery member. The coating can have one or more grooves into which the endoprosthesis can be at least partially disposed. The coating can have a deformable surface against which the endoprosthesis can be at least partially disposed.

In certain embodiments, the secondary member can include a seating member (e.g., a plurality of seating members). In some embodiments, the secondary member can include windings of a material supported by the delivery member, for example, windings having a durometer of from about 65 A to about 55 D.

In certain embodiments, the system includes a bumper connected to the delivery member, the bumper being proximal to the endoprosthesis. The bumper can be configured to substantially prevent proximal movement of the endoprosthesis when the sheath is moved proximally.

In some embodiments, the system further includes a proximal sub-bumper located proximal to the bumper and attached to the delivery member, and a distal sub-bumper located distal to the bumper and attached to the delivery member. The bumper has a lumen having a diameter larger than a diameter of the delivery member and through which the delivery member extends. The proximal and distal sub-bumpers each have a diameter that is larger than the diameter of the lumen in the bumper.

In some embodiments, the system can include a tip (e.g., a bullet-shaped tip) connected to the delivery member, the tip being distal to the endoprosthesis. The tip can be configured to substantially prevent distal movement of the endoprosthesis when the sheath is moved distally.

In some embodiments, the first material can be a wire. In some embodiments, the first article can include a metal, an alloy, or a plastic. In some embodiments, the second material can include rubber, synthetic rubber, latex, polyurethane/silicone combinations, [poly(styrene-b-isobutylene-b-styrene)], or poly-(ether block amide).

Embodiments can include one or more of the following advantages.

In some embodiments, the endoprosthesis delivery systems may enable the prosthesis to be partially deployed and/or partially expanded and then retracted into the catheter to be repositioned and/or removed.

In certain embodiments, the outer diameter of the system may be reduced, for example, to a microcatheter size to enable delivery and deployment of endoluminal devices to lumens having a small diameter.

In some embodiments, the delivery system may have enhanced flexibility for traveling through tortuous pathways in a subject's body.

Other features and advantages are apparent from the description, drawings and claims.

DESCRIPTION OF DRAWINGS

Like reference symbols in the various drawings indicate like elements.

DETAILED DESCRIPTION

Figure 1:
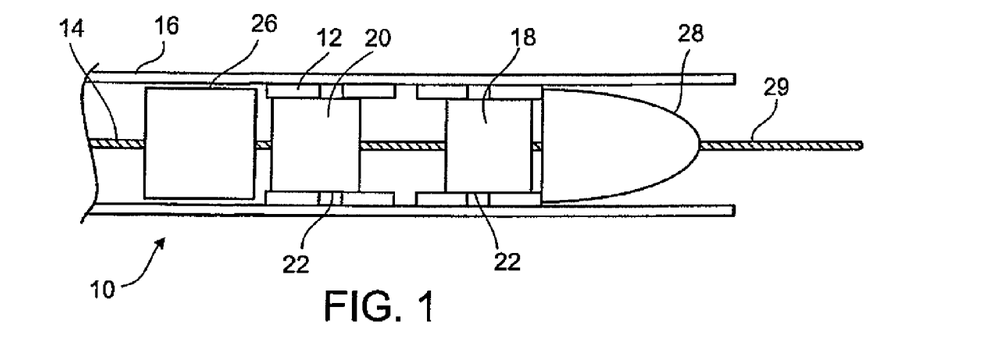
FIG. 1 is a partial cross-sectional view of an embodiment of an implantable medical endoprosthesis delivery system.

FIG. 1 shows an implantable medical endoprosthesis delivery system 10 including a delivery wire 14 (e.g., a guide wire) within a catheter 16, and a stent 12 disposed between the delivery wire 14 and the catheter 16. Stent 12 is typically a self-expanding stent, and is typically contained in the catheter 16, which constrains stent 12 from expanding into its fully-expanded state. A first seating member 18 and a second seating member 20 are disposed on the delivery wire 14 between the delivery wire 14 and the stent 12. The first and second seating members 18 and 20 each have a diameter such that seating surfaces 22 on each of the first and second members 18 and 20 contacts the stent 12 while the stent 12 is disposed within the catheter 16. The seating members 18 and 20 are configured, in conjunction with the configurations of the stent 12 and the catheter 16, such that, when the stent is disposed on the seating members 18 and 20 and is disposed within the catheter 16, the stent 12 will preferentially remain disposed on the seating members 18 and 20 when catheter 16 and seating members 18 and 20 are moved with respect to each other. In certain embodiments, this may be the result of a friction fit created by the contact between the stent 12 and the seating members 18 and 20. For example, the seating surfaces 22 may have a coefficient of friction higher than that of the inner surface of the catheter 16. In certain embodiments, the seating members 18 and 20 and/or the seating surfaces 22 may be formed of a material which is at least partially deformable, for example, a soft, tacky, resilient, or elastomeric material, for example, a material having a durometer of from about 55 A to about 100 A (e.g., from about 60 A to about 90 A, from about 65 A to about 85 A, or from about 70 A to about 80 A) and/or from about 15 D to about 55 D (e.g., from about 20 D to about 50 D, from about 25 D to about 45 D, or from about 30 D to about 40 D). The durometer, or hardness, is measured in accordance with ASTM 2240. In some embodiments, the stent is at least slightly pressed into the at least partially deformable seating member and/or seating surface. Exemplary materials include rubber, synthetic rubber, latex, polyurethane/silicone combinations such as, for example, Elast-Eon™ polymers by AorTech, and other polymers such as, for example, [poly(styrene-b-.isobutylene-b-styrene)] ("SIBS"), or poly-(ether block amide), (e.g., PEBAX®).

In certain embodiments, the seating surface may have one or more grooves into which the stent can be at least partially deployed. The stent 12, as a result of the seating members and/or seating surfaces, remains substantially stationary with respect to the delivery wire 14 when the catheter 16 moves proximally or distally with respect to the delivery wire 14. Likewise, while when the delivery wire 14 moves proximally or distally, the stent 12 remains substantially stationary with respect to the delivery wire 14. Exemplary materials for forming the seating members 18 and 20 and/or the seating surfaces 22 include rubber, synthetic rubber, latex, polyurethane/silicone combinations such as, for example, Elast-Eon™ polymers, and other polymers such as, for example, [poly(styrene-b-.isobutylene-b-styrene)] ("SIBS"), or poly-(ether block amide), (e.g., PEBAX®). The seating surfaces 22 may be formed of the same or a different material than the seating members 18, 20, and may make up an additional layer or component of the seating members 18, 20 or may simply be the outer surface of each seating member rather than an additional component.

As illustrated in FIG. 1, the implantable medical endoprosthesis delivery system 10 may further include a proximal bumper 26 disposed on the delivery wire 14 proximal to the stent 12. The proximal bumper 26 is configured to substantially prevent proximal movement of the stent 12 when the catheter 16 is moved proximally. The proximal bumper 26 may also serve to help in pushing the stent 12 through the catheter 16 where such is desired. A bullet-shaped tip 28 is connected to the delivery wire 14 distal of the stent 12. The tip 28 is configured to substantially prevent distal movement of the stent 12 when the catheter 16 is moved distally and to assist in the delivery of the catheter 16, preloaded with the stent 12, through body lumens to the position at which the stent 12 is to be deployed. Optionally, the delivery wire 14 can extend through the tip 28 such that a distal portion 29 of the delivery wire 14 extends beyond the tip 28 distally, for example, through a lumen (not illustrated) in the tip 28.

Figure 2A:
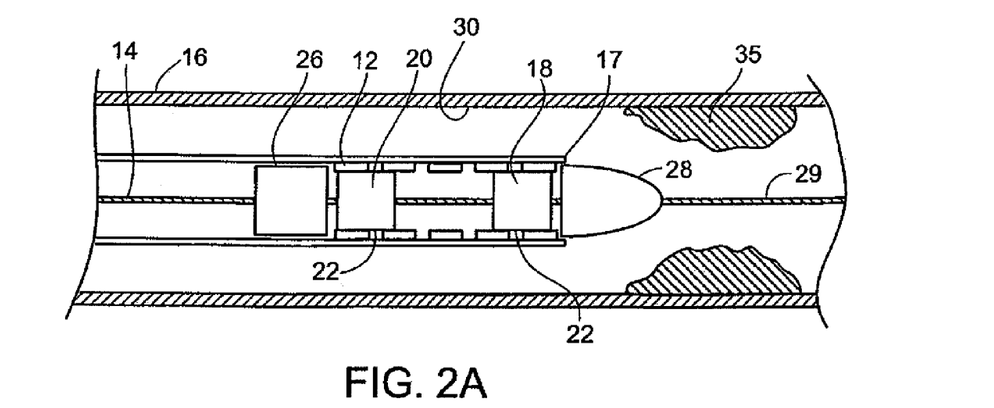
FIGS. 2A-C are diagrams of an embodiment of a method.
Figure 2B:
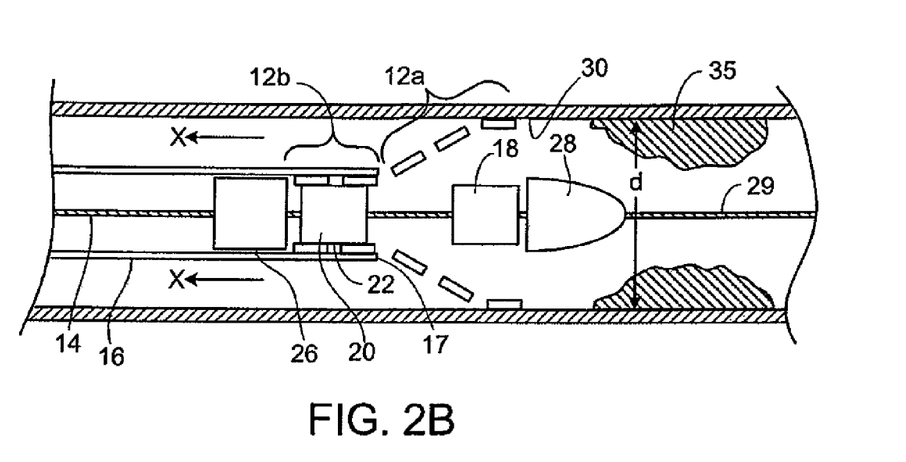
Figure 2C:
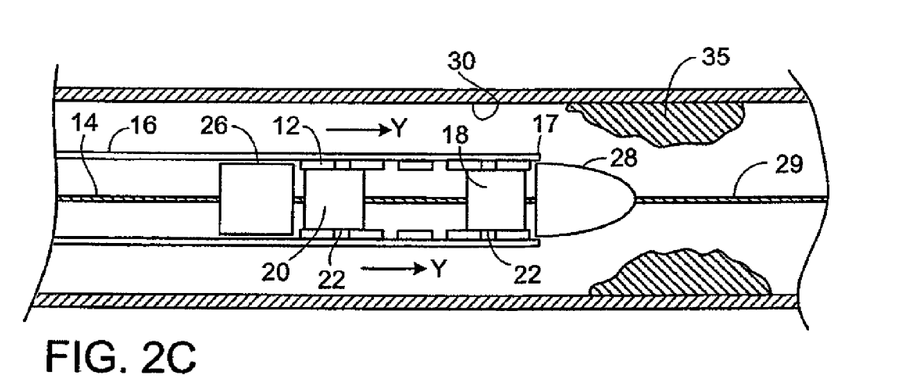
Figure 3A:
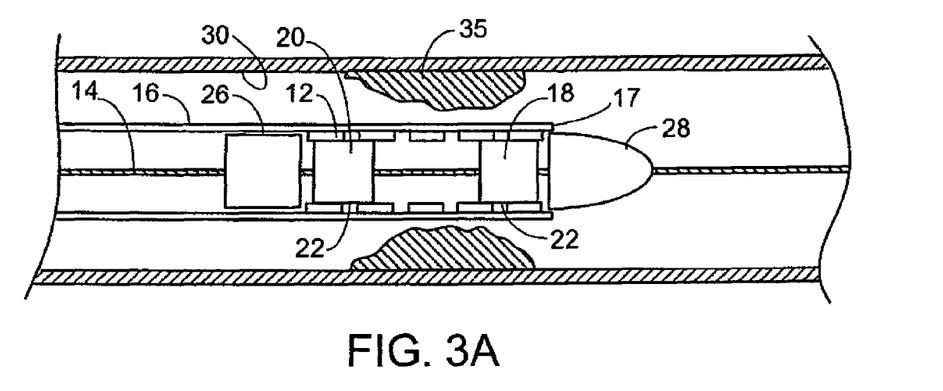
FIGS. 3A-C are diagrams of an embodiment of a method.
Figure 3B:
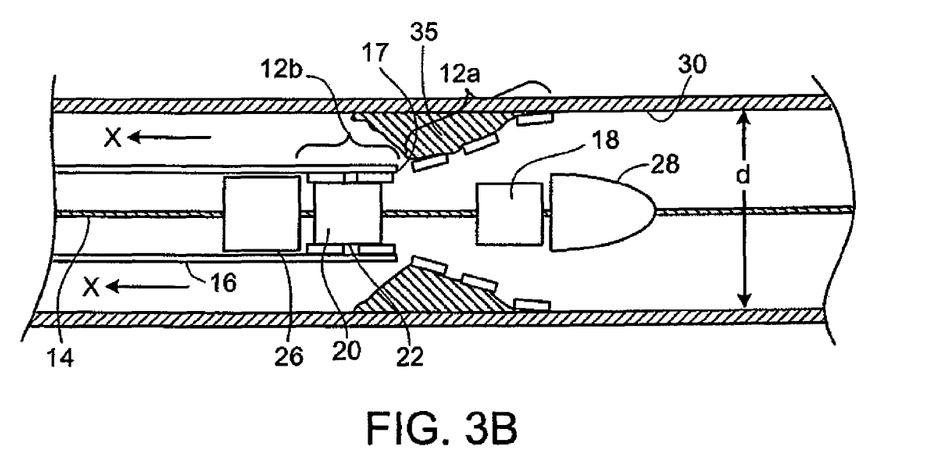
Figure 3C:
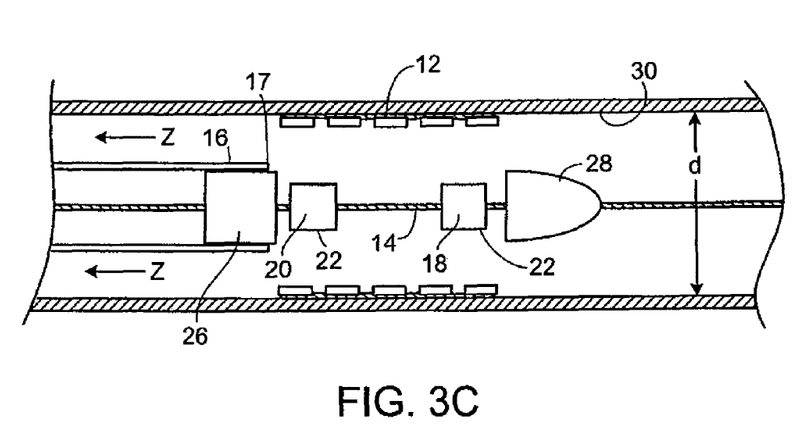

FIGS. 2 and 3 illustrate a method utilizing implantable medical endoprosthesis delivery system 10. In general, implantable medical endoprosthesis delivery system 10 is used as follows. System 10 is positioned within a body lumen 30 (e.g., an artery) at a desired location, for example, adjacent an occlusion 35. Initially, as seen in FIGS. 2A and 3A, the stent 12 is contained in an unexpanded state within the catheter 16 at a distal end 17 of the catheter 16. The catheter 16 serves to restrain the stent 12 from self-expanding at this point. The catheter 16 is withdrawn (moved proximally) as indicated by arrows X in FIGS. 2B and 2C, to expose or uncover a distal portion 12a of the stent 12. When the distal portion 12a of the stent 12 is uncovered (and thereby unrestrained from self-expansion), the distal portion self-expands towards a deployed diameter d, which is the diameter of the stent 12 when expanded in the body lumen 30. Typically, the deployed diameter d is less than the diameter to which the stent 12 would expand absent the body lumen 30. In this fashion, the stent 12 can continue to exert radial force, which can help to force open the occlusion and/or to maintain the position of the stent 12 within the body lumen 30.

At this point, the physician may desire to reposition the stent and/or system within lumen 30, e.g., to select a more suitable location for the stent or to correct for errors in positioning resulting from the partial deployment of the stent. Optionally, the physician may desire to entirely re-sheath and/or remove the stent (e.g., to replace it with a stent of, for example, a larger or smaller expanded diameter). Re-sheathing of the stent is possible, due at least in part to the presence of the second seating member 20. The catheter 16 can, as illustrated in FIG. 2C, be advanced (moved distally as indicated by arrows Y) to re-cover at least some of the expanded distal portion 12a of the stent 12 and depose the at least some of the expanded distal portion 12a of the stent 12 within the catheter 16.

Alternatively, as illustrated in FIG. 3C, the catheter 16 can be further withdrawn as indicated by arrows Z to expose or uncover the remaining proximal portion 12b of stent 12. Stent 12 can expand to the extent that the body lumen 30 permits once so exposed.

Figure 4A:
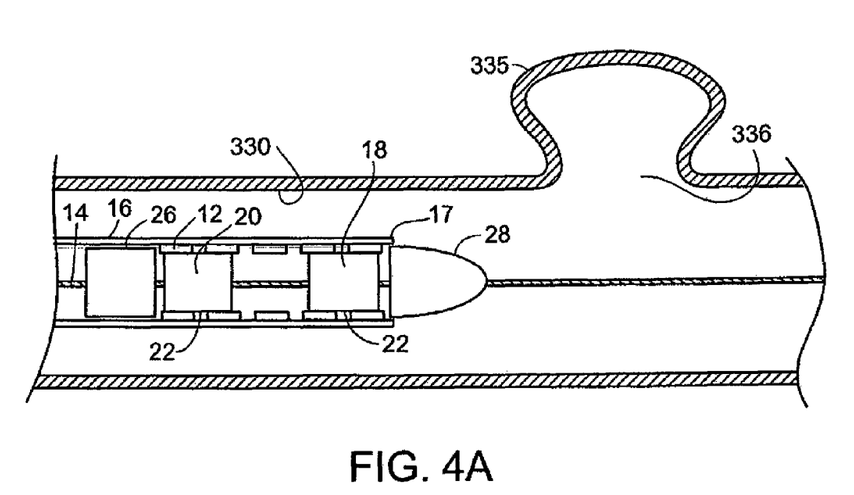
FIGS. 4A-C are diagrams of an embodiment of a method.
Figure 4B:
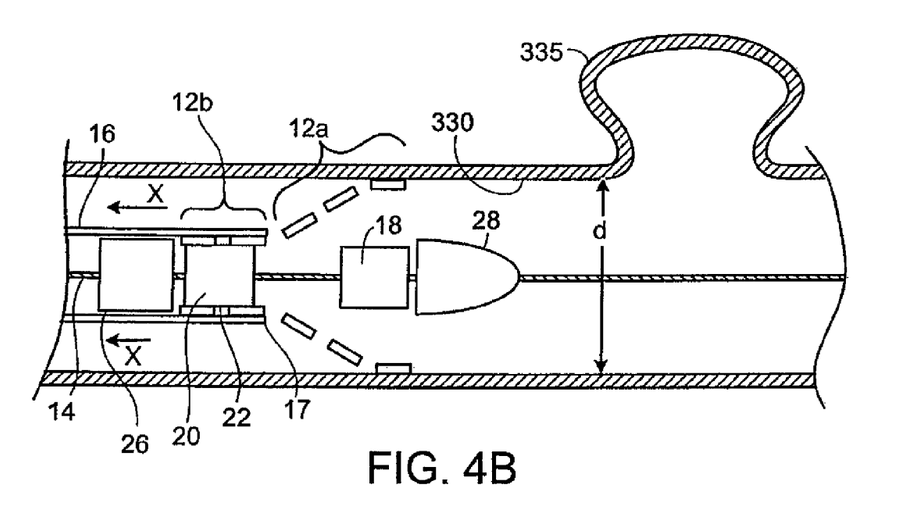
Figure 4C:
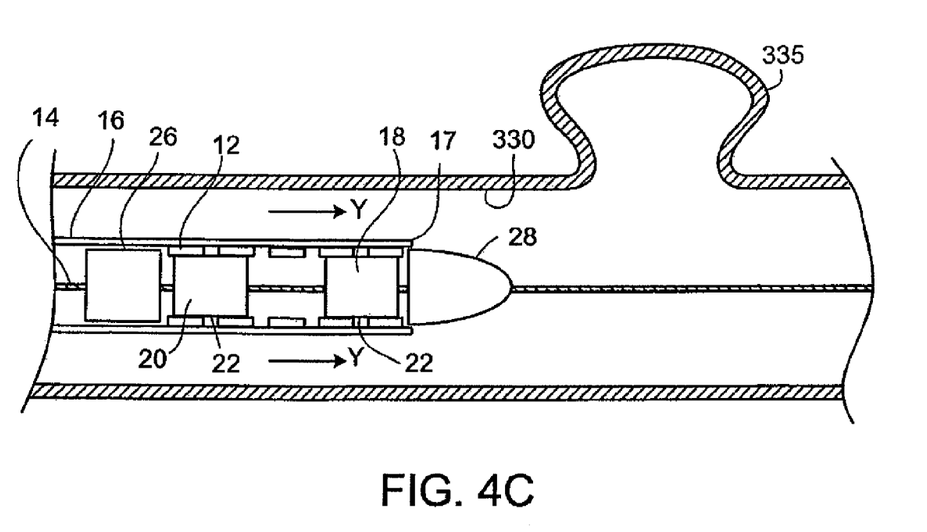
Figure 5A:
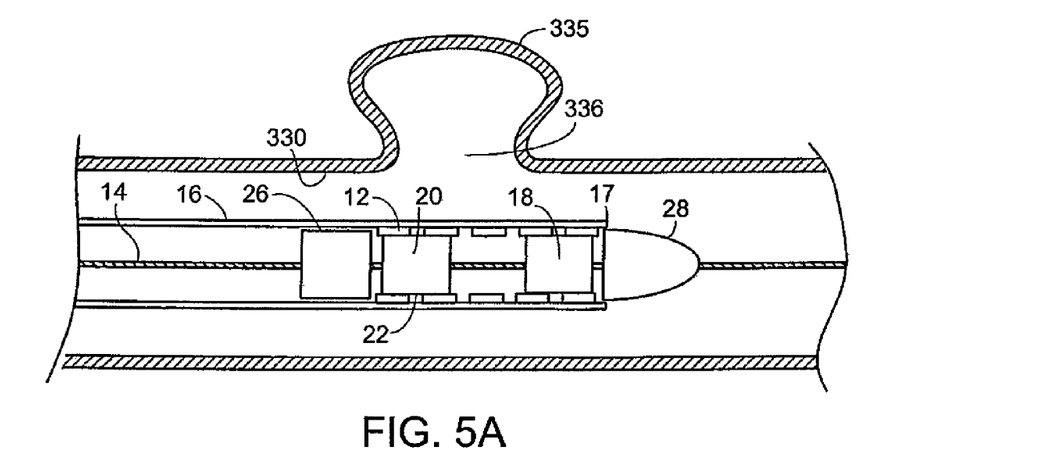
FIGS. 5A-C are diagrams of an embodiment of a method.
Figure 5B:
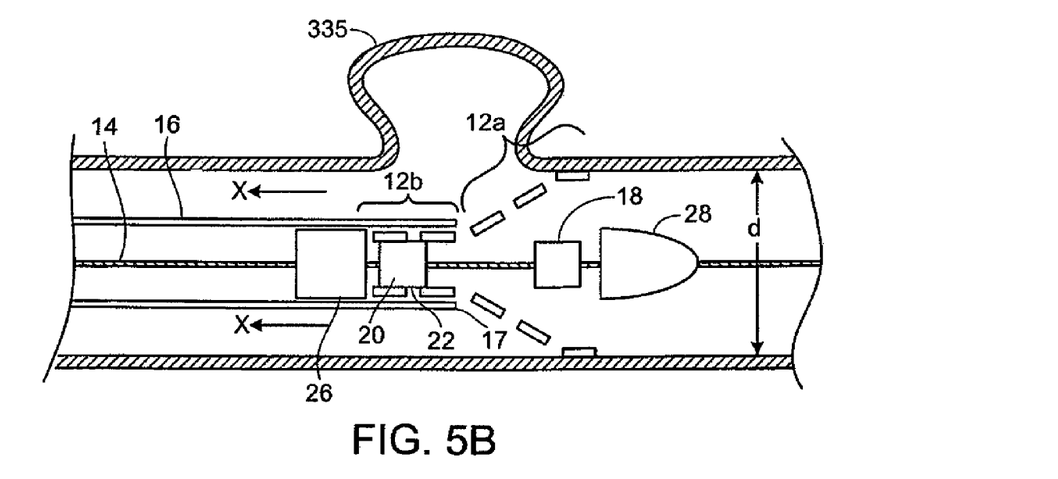
Figure 5C:
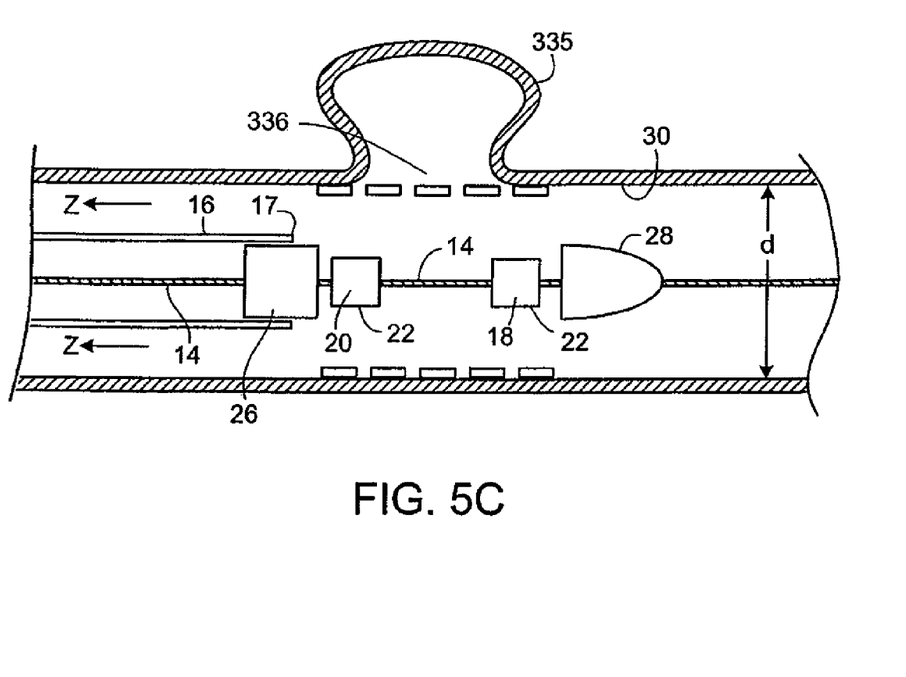

FIGS. 4 and 5 illustrate a similar method, utilizing implantable medical endoprosthesis delivery system 10 to block the opening of an aneurysm 335 and/or strengthen a vessel at the site of aneurysm 335. System 10 is positioned within a body lumen 330 (e.g., an artery) at a desired location, for example, adjacent aneurysm 335. Initially, as seen in FIGS. 4A and 5A, the stent 12 is contained in an unexpanded state within the catheter 16 at a distal end 17 of the catheter 16. The catheter 16 is withdrawn (moved proximally) as indicated by arrows X in FIGS. 4B and 5B, to expose or uncover a distal portion 12a of the stent 12. When the distal portion 12a of the stent 12 is uncovered (and thereby unrestrained from self-expansion), the distal portion self-expands towards a deployed diameter d, which is the diameter of the stent 12 when expanded in the body lumen 330. At this point, the physician may desire to reposition the stent and/or system within lumen 330 or to entirely re-sheath and remove the stent and replace it with a stent of, for example, a larger or smaller expanded diameter. The catheter 16 can, as illustrated in FIG. 4C, be advanced (moved distally as indicated by arrows Y) to re-cover at least some of the expanded distal portion 12a of the stent 12 and depose the at least some of the expanded distal portion 12a of the stent 12 within the catheter 16.

Should the physician determine that the stent 12 is properly positioned within lumen 330, as illustrated in FIG. 5C, the catheter 16 can be further withdrawn as indicated by arrows Z to expose or uncover the remaining proximal portion 12b of stent 12. Stent 12 can then expand to the extent that the body lumen 330 permits once so exposed, thereby at least partially occluding the opening 336 to the aneurysm 335.

Figure 6:
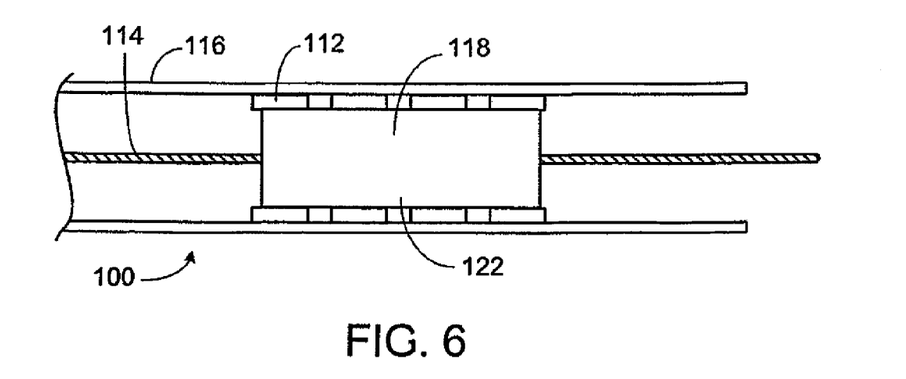
FIG. 6 is a partial cross-sectional view of an embodiment of an implantable medical endoprosthesis delivery system.

[In the embodiment illustrated in FIG. 6, an implantable medical endoprosthesis delivery system 100 has a delivery wire 114 within catheter 116, and a stent 112 disposed between the delivery wire 114 and the catheter 116. A coating 118 is disposed on the delivery wire 114 (e.g., a guide wire) between the delivery wire 114 and the stent 112, with a coating surface 122 contacting the stent 112. In general, the coating surface 122 is formed of a material that presses against or into the stent to force the stent to travel longitudinally, relative to the catheter, with the delivery wire. The coating may in certain embodiments be formed of a liquid or fluid material placed on or applied to the exterior of the wire and allowed to harden on the exterior of the wire, for example, sprayed on, brushed on, shrink-wrapped, and/or hot-dipped. Generally, the thickness of the coating is selected based on the catheter inner diameter, stent thickness, and delivery wire diameter. In some embodiments, the coating has a thickness of no less than about 0.05 mm (e.g., no less than about 0.10 mm, no less than about 0.15 mm, or no less than about 0.20 mm) and/or no more than about 0.25 mm (e.g., no more than about 0.20 mm, no more than about 0.15 mm, or no more than about 0.10 mm).

The coating may in certain embodiments be a sleeve or a cylindrical plug of material having a central bore for receiving the delivery wire. The sleeve or plug grips the delivery wire with sufficient force to ensure that it travels with the delivery wire. The coating may be a polymer coating, for example a thermoplastic coating (e.g., ElastEon™) or may be a rubber, synthetic rubber, SIBS, or poly-(ether block amide) (e.g., PEBAX®). The coating thickness is generally selected such that the coating will contact the endoprosthesis while the prosthesis is disposed within the delivery catheter and may be, for example, no less than about 3 μm thick (e.g., no less than about 50 μm thick, no less than about 100 μm thick, no less than about 150 μm thick, no less than about 200 μm thick, no less than about 250 μm thick, no less than about 300 lam thick, no less than about 350 μm thick, no less than about 400 μm thick, no less than about 450 μm thick, no less than about 500 μm thick, no less than about 550 μm thick, no less than about 600 μm thick, or no less than about 650 μm thick) and/or no more than about 700 μm thick (e.g., no more than about 650 μm thick, no more than about 600 μm thick, no more than about 550 μm thick, no more than about 500 μm thick, no more than about 450 μm thick, no more than about 400 μm thick, no more than about 350 μm thick, no more than about 300 μm thick, no more than about 250 μm thick, no more than about 200 μm thick, no more than about 150 μm thick, no more than about 100 μm thick, or no more than about 50 μm thick). This provides for delivery wire/coating combinations having a diameter of no less than about 0.1 mm (e.g., no less than about 0.2 mm, no less than about 0.4 mm, no less than about 0.6 mm, no less than about 0.8 mm, or no less than about 1 mm) and/or no more than about 1.2 mm (e.g., no more than about 1 mm, no more than about 0.8 mm, no more than about 0.6 mm, no more than about 0.4 mm, or no more than about 0.2 mm). The coating 118 and the coating surface 122 may be formed of the same or of different materials. The coating 118 and the coating surface 122 may be contiguous, whereby the coating surface is formed of the outward-facing surface of the coating. The coating and coating surface are configured to retain the stent 112 in a substantially motionless position relative to the delivery wire 114 when the catheter 116 is moved proximally or distally and/or when the delivery wire 114 is moved proximally or distally.

Figure 7:
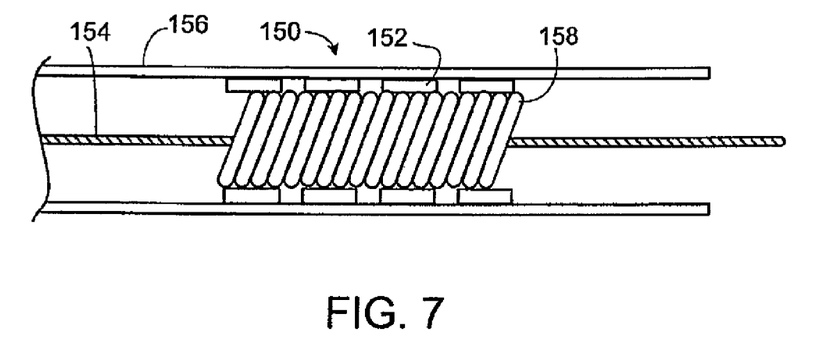
FIG. 7 is a partial cross-sectional view of an embodiment of an implantable medical endoprosthesis delivery system.
Figure 8:
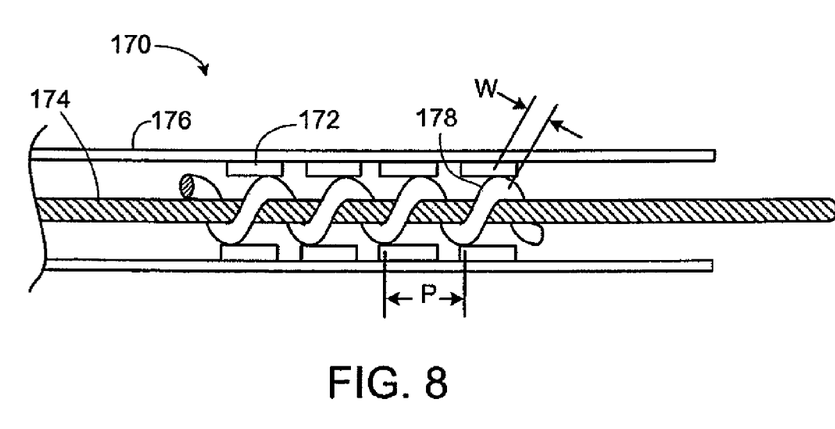
FIG. 8 is a partial cross-sectional view of an embodiment of an implantable medical endoprosthesis delivery system.

FIGS. 7 and 8 illustrate other embodiments of implantable medical endoprosthesis delivery systems. An implantable medical endoprosthesis delivery system 150, illustrated in FIG. 5, has a delivery wire 154 within catheter 156, and a stent 152 disposed between the delivery wire 154 and the catheter 156. Windings 158 are disposed on the delivery wire 154 between the delivery wire 154 and the stent 152. The windings may be formed of a single strand of winding material, or optionally may be formed of multiple strands of winding material, for example, two, three or more strands of winding material. The windings 158 may be formed from a winding material including a resilient material, e.g., a polymer, for example, ElastEon™, poly-(ether block amide), (e.g., PEBAX®) or SIBS. The windings may be formed from an elastomeric material, e.g., a material having a durometer of at from about 65 A to about 55 D. The windings may extend substantially along the full length of the endoprosthesis, or may extend along a portion of the endoprosthesis. Multiple sections of windings may be included, e.g., two, three or more sections each supporting a portion of the endoprosthesis. The windings 158 are sized to provide a windings diameter sufficient to apply a radial force to the stent 152 so that the stent 152 forms a friction fit with the catheter 156 to retain the stent 152 in a substantially motionless position relative to the delivery wire 154 when the catheter 156 is moved proximally or distally and/or when the delivery wire 154 is moved proximally or distally. In certain embodiments, the windings may form a mechanical grip with the struts of the stent, whereby the struts are at least partially disposed within the spaces between the windings.

In general, the windings may in certain embodiments have an average width (e.g., diameter, when the windings are cylindrical) of no less than about 3 μm (e.g., no less than about 50 μm, no less than about 100 μm, no less than about 150 μm, no less than about 200 μm, no less than about 250 μm, no less than about 300 μm, no less than about 350 μm, no less than about 400 μm, no less than about 450 μm, no less than about 500 μm, no less than about 550 μm, no less than about 600 μm, or no less than about 650 μm) and/or no more than about 700 μm (e.g., no more than about 650 μm, no more than about 600 μm, no more than about 550 μm, no more than about 500 μm, no more than about 450 μm, no more than about 400 μm, no more than about 350 μm, no more than about 300 μm, no more than about 250 μm, no more than about 200 μm, no more than about 150 μm, no more than about 100 μm, or no more than about 50 μm). The windings may in certain embodiments have an average pitch (the length, measured longitudinally, of one full turn of the windings around the delivery wire) of no more than about 10 mm (e.g., no more than about 1 mm, no more than about 0.1 mm, or no more than about 0.05 mm) and/or no less than about 0.025 mm (e.g., no less than about 0.05 mm, no less than about 0.1 mm, or no less than about 1 mm). In certain embodiments, the windings may be placed on the delivery wire such that they are spaced apart from each other, which may impart greater flexibility to the delivery system. For example as illustrated in FIG. 8, the ratio of an average pitch p of the windings to an average width w of the windings may be at least about 2 (e.g., at least about 2.5, at least about 3, at least about 3.5, at least about 4, at least about 4.5), and may be at most about 5 (e.g., at most about 4.5, at most about 4, at most about 3.5, at most about 3, at most about 2.5), and may be between about 2 and about 5 (e.g., between about 2.5 and about 4.5, between about 3 and about 4).

The windings in certain embodiments extend for an overall length of no more than about 35 mm (e.g., no more than about 30 mm, no more than about 25 mm, or no more than about 20 mm) and/or no less than about 15 mm (e.g., no less than about 20 mm, no less than about 25 mm, or no less than about 30 mm). In some embodiments, multiple sections of windings can be employed. Where multiple sections of winding are included, each section may have the same or different winding pitch, winding width, and/or ratio of the average pitch to the average width of the windings.

Figure 9A:
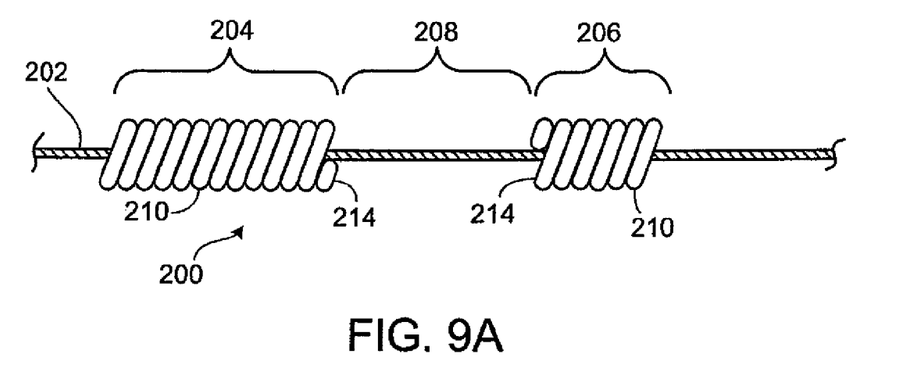
FIG. 9A is an embodiment of a guidewire.

FIG. 9A shows a delivery wire 200 (e.g., a guidewire) which includes a wire 202 having a first portion 204, a second portion 206, and a third portion 208 disposed between the first and second portions 204 and 206, respectively. Windings 210 are disposed on the first portion 204 and the second portion 206 but the third portion 208 has no windings disposed thereupon. The windings 210 are typically formed of a material that is different from the material that forms the wire 202. Generally, windings 210 may be any suitable material for achieving the desired stiffness/flexibility of the delivery wire, and may include, for example, metals, metal oxides, polymers, or plastics. The windings 210 are generally sized to provide stent-contacting surfaces 214 that contact both ends of stent 212 so that the stent 212 is retained in a substantially motionless position relative to the delivery wire 200 when the catheter 216 is moved proximally or distally and/or when the delivery wire 200 is moved proximally or distally. In certain embodiments, the windings may have a diameter of no less than about 0.02 mm (e.g., no less than about 0.025 mm, no less than about 0.03 mm, no less than about 0.05 mm, or no less than about 1 mm) and/or no more than about 1.5 mm (e.g., no more than about 1 mm, no more than about 0.05 mm, no more than about 0.03 mm, no more than about 0.025 mm, or no more than about 0.02 mm). This provides for delivery wires having an overall diameter, inclusive of the windings, of no less than about 0.1 mm (e.g., no less than about 0.2 mm, no less than about 0.3 mm, no less than about 0.4 mm, no less than about 0.5 mm, no less than about 0.6 mm, no less than about 0.7 mm, no less than about 0.8 mm, or no less than about 0.9 mm) and/or no more than about 1.0 mm (e.g., no more than about 0.9 mm, no more than about 0.8 mm, no more than about 0.7 mm, no more than about 0.6 mm, no more than about 0.5 mm, no more than about 0.4 mm, no more than about 0.3 mm, no more than about 0.2 mm, or no more than about 0.1 mm). The third portion 208 is generally configured to be at least as long as or slightly longer than the implantable endoprosthesis that is to be disposed around the third portion 208. For example, in some embodiments, the third portion has a length of at least about 0.5 cm (e.g., at least about 1 cm, at least about 2 cm, at least about 3 cm, at least about 4 cm, at least about 5 cm, at least about 6 cm, at least about 8 cm, or at least about 10 cm) and/or no more than about 15 cm (e.g., no more than about 10 cm, no more than about 8 cm, no more than about 6 cm, no more than about 5 cm, no more than about 4 cm, no more than about 3 cm, no more than about 2 cm, or no more than about 1 cm).

Figure 9B:
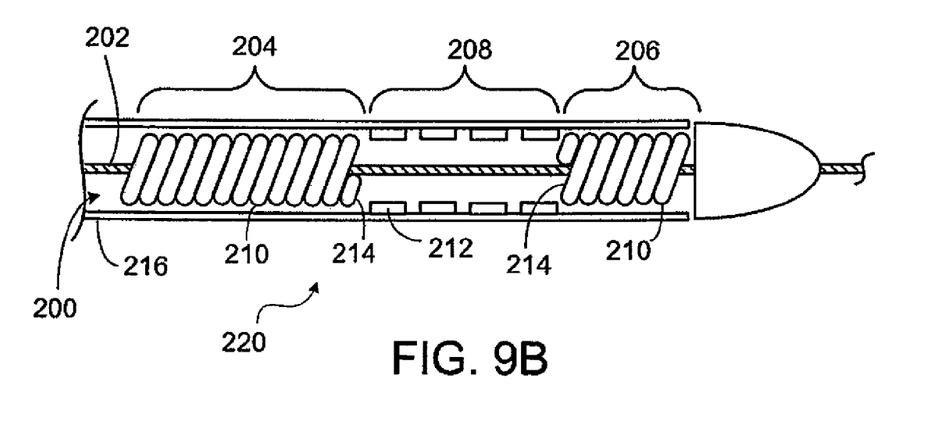
FIG. 9B is an embodiment of an implantable medical endoprosthesis delivery system including the guidewire of FIG. 9A.

An implantable medical endoprosthesis delivery system 220 including the delivery wire 200 is illustrated in FIG. 9B. A stent 212 is disposed between the first portion 204 of the delivery wire 200 and a catheter 216. The windings 210 each have a stent-contacting surface 214 disposed on the end of the windings 210 that face the third section 208 of the delivery wire 200. The third portion 208 is sized to permit rotation or torque of the delivery wire 200 while applying substantially no torque to the stent 212.

In some embodiments, the delivery wire may further include a proximal bumper, a distal tip or bumper, or both, on the first and/or second portions and typically at the edge of the proximal and distal portions nearest the intermediate portion. Such bumper or bumpers may contact the stent in lieu of a stent-contacting surface of the windings, and would serve the same purpose, namely to hold the stent substantially motionless (in a proximal or distal direction) relative to the delivery wire. In some embodiments, the third portion of the delivery wire may have windings disposed thereupon, provided that the diameter of the third portion, inclusive of the optional windings, remains small enough to permit the delivery wire to be torqued without imparting torque to the stent. Such a configuration may be desirable where additional stiffness is desired in the delivery wire, for example, where the endoprosthesis is particularly long (e.g. at least 25 mm long, at least 30 mm long, at least 35 mm long, at least 40 mm long, or at least 45 mm long).

Figure 10A:
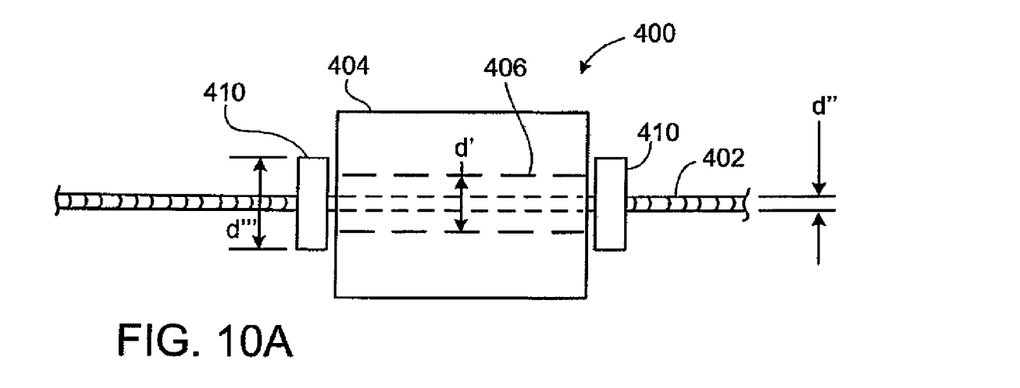
FIG. 10A is a cross-sectional view of an embodiment of a bumper on a delivery wire.
Figure 10B:
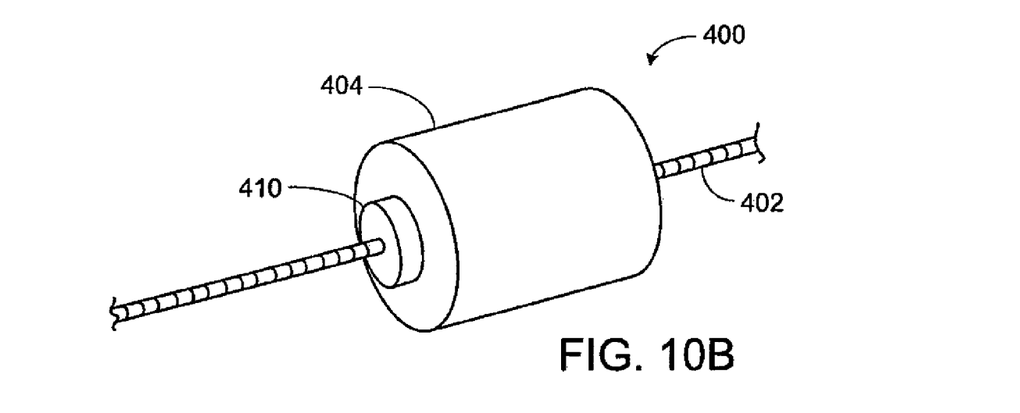
FIG. 10B is a perspective view of the embodiment of FIG. 11A.

FIGS. 10A and 10B illustrate a delivery wire 400 (e.g., a guidewire) including a wire 402 having a member 404 (e.g., a seating member or a bumper) disposed thereon, in which the wire 402 can be rotated without causing the member 404 to rotate. The member 404 has a lumen 406 through which the wire 402 passes. The lumen 406 has a diameter d' that is large enough to allow the wire 402 to rotate within the lumen 406 without applying substantial amounts of (e.g., without applying any) torque to the member 404 (e.g., d' is larger than a diameter d" of the wire 402). A pair of sub-bumpers 410 are attached (e.g., adhered) to the wire 402 at positions proximal and distal the member 404. The sub-bumpers 410 each have a diameter d''' that is larger than the diameter d' of the lumen 406 in member 404, such that the sub-bumpers can prevent the member 404 from moving proximally or distally along the wire 402 beyond either of the sub-bumpers 410. In this fashion, the member 404 is retained laterally at a single position on wire 402, but is not subject to torque when wire 402 is rotated (e.g., to steer wire 402 through a body lumen). The sub-bumpers 410 are attached to the wire 402 such that the sub-bumpers 410 move laterally and rotationally with the wire 402. The diameter d''' of the sub-bumpers 410 is smaller than an outer diameter of the member 404.

Figure 11:
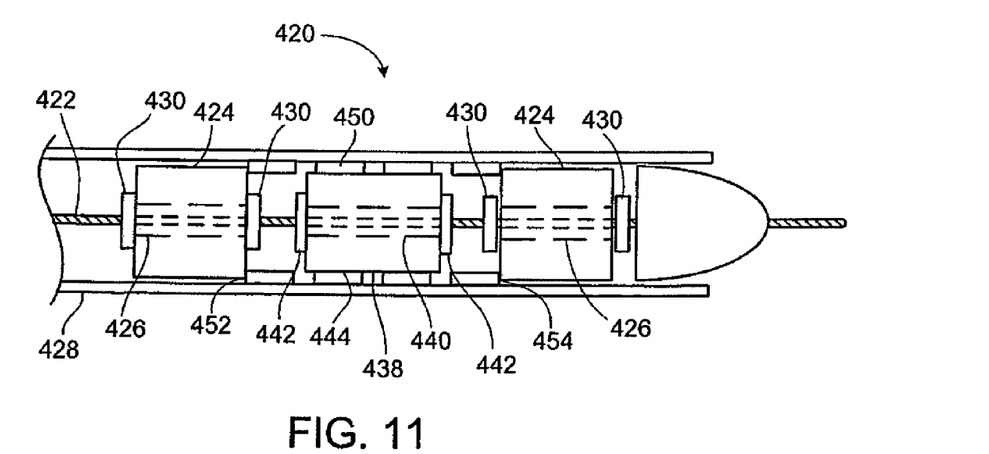
FIG. 11 is a partial cross-sectional view of an implantable medical endoprosthesis delivery system.

FIG. 11 illustrates an implantable medical endoprosthesis delivery system 420 that includes bumpers stent seating members that are not subject to torque when the delivery wire is rotated. The system 420 includes a pair of bumpers 424, each having a lumen 426 through which a wire 422 passes, the lumen 426 having a diameter larger than the diameter of the wire 422. The bumpers are held in place laterally by two pairs of sub-bumpers 430, each attached to the wire 422 such that they move laterally and rotationally along with the wire 422. The sub-bumpers 430 have a diameter larger than the diameter of the lumen 426 of the bumpers 424. The bumpers 424 are spaced apart from one another such that a stent 450 can be located between the bumpers 424. The stent 450 and the delivery wire 422 are contained in a catheter 428, which constrains the stent 450 from expanding into its fully-expanded state.

A seating member 438 is disposed between the wire 422 and the stent 450. The seating member 438 has a lumen 440 through which the wire 422 passes, the lumen 440 having a diameter larger than the diameter of the wire 422. The seating member 438 is held in place laterally by two pairs of sub-bumpers 442, each attached to the wire 422 such that they move laterally and rotationally along with the wire 422. The sub-bumpers 442 have a diameter larger than the diameter of the lumen 440 of the seating member 438.

The seating member 438 has a diameter of sufficient size such that an outer (seating) surface 444 on the seating member 442 contacts the stent 450 while the stent 450 is disposed within the catheter 428. The bumpers 424 each have a diameter such that the bumper can contact a proximal edge 452 or a distal edge 454 of the stent 450. Each of the sub-bumpers 430 and 442 are sized to be larger than the lumen of the member (bumper 424 or seating member 438) that they abut while being small enough to avoid subjecting either the stent 450 or the catheter 428 to torque upon rotation of the wire 422.

Figure 12:
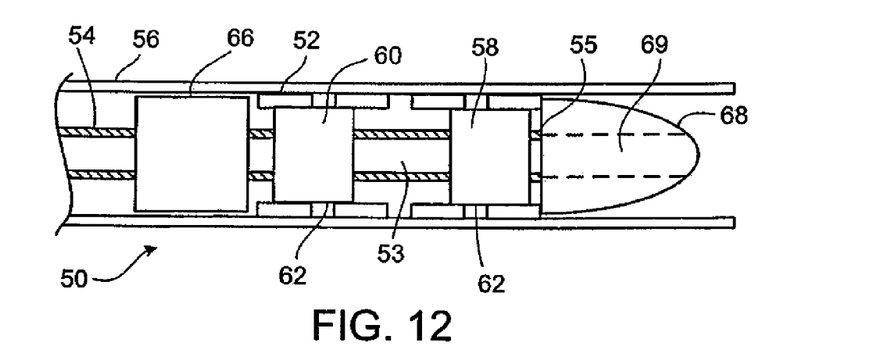
FIG. 12 is a partial cross-sectional view of an embodiment of an implantable medical endoprosthesis delivery system.

[In certain embodiments, an implantable medical endoprosthesis may be delivered using a delivery catheter rather than a delivery wire. One such embodiment is illustrated in FIG. 12, in which an implantable medical endoprosthesis delivery system 50 includes a delivery catheter 54 within outer catheter 56, and a stent 52 disposed between the delivery catheter 54 and the outer catheter 56. A first seating member 58 and second seating member 60 are disposed on the delivery catheter 54 between the delivery catheter 54 and the stent 52. The first and second seating members 58 and 60 each have a diameter such that seating surfaces 62 on each of the first and second members 58 and 60 contacts the stent 52. The first and second seating members 58 and 60 are configured such that, when the outer catheter 56 moves proximally or distally with respect to the delivery catheter 54, the stent 52 remains substantially stationary with respect to the delivery catheter 54, while when the delivery catheter 54 moves proximally or distally, the stent 52 remains substantially stationary with respect to the delivery catheter 54. The first and second seating members 58 and 60 may be made of any of the materials disclosed above, and may include seating surfaces in accordance with those described above. A proximal bumper 66 is disposed on the delivery catheter 54 proximal to the stent 52 and is configured to substantially prevent proximal movement of the stent 52 when the outer catheter 56 is moved proximally. The proximal bumper 66 may also serve to help in pushing the stent 52 through the outer catheter 56 where such is desired. A bullet-shaped tip 68 is connected to a distal end 55 of the delivery catheter 54 distal of the stent 52 and is configured to substantially prevent distal movement of the stent 52 when the outer catheter 56 is moved distally. The bullet-shaped tip 68 includes a tip lumen 69 extending longitudinally therethrough to form, in conjunction with a lumen 53 in delivery catheter 54, a lumen, e.g., through which a guidewire (not here illustrated) can extend.

While certain embodiments have been described, others are possible.

[For example, in certain embodiments, a seating member may extend distally beyond the distal end of the delivery device and itself form a tip, e.g., a bullet shaped tip.

As another example, the delivery wire can in certain embodiments comprise a metal, an alloy (e.g., a stainless steel or Nitinol), or a polymer (e.g., a plastic).

As another example, in certain embodiments, the delivery member can be formed of a tube, e.g., a tube having a spiral tube, attached (e.g., by adhesive or by weld) to the outside of the tube. As another example, the delivery member can be a slotted hypotube, a rigid or semirigid tube having slots cut into it (e.g., by mechanical cutting or laser ablation). Such a delivery device can include an inner lumen while maintaining more flexibility than an unslotted tube.

As another example, in certain embodiments, the catheter or sheath in which the endoprosthesis is contained may be a microcatheter, e.g., the catheter may have a diameter of not more than about 5 french (e.g., not more than about 4 french, not more than about 3.5 french, not more than about 3 french, not more than about 2.5 french, not more than about 2.3 french, not more than about 2 french).

As another example, in certain embodiments, an adhesive may be interposed between the delivery wire or catheter and the seating members, coatings, and/or windings to ensure that the seating device travels with the delivery device.

As another example, in certain embodiments, a seating member can be a balloon that could be at least partially inflated to achieve a friction fit between itself and the endoprosthesis. Such a balloon could optionally remain uninflated unless retraction of a partially-deployed endoprosthesis was desired, at which point it could be at least partially inflated to achieve a friction fit.

As another example, in certain embodiments, the endoprostheses, delivery wires, catheters and/or guidewires may include one or more radiopaque materials, for example, one or more bands of radiopaque materials.

As another example, in certain embodiments, any of the seating components (seating members, seating surfaces, coatings, wrappings, windings) the seating members can comprise a resilient and/or deformable material such that the endoprosthesis can press into it, forming a releasable mechanical grip with the seating member. For example, the seating component may have a durometer of no more than 55 D (e.g., no more than 65 A). Exemplary resilient materials include, for example, ElastEon™, SIBS, or poly-(ether block amide), (e.g., PEBAX®).

As another example, the seating surface may have a tacky consistency to which the endoprosthesis adheres, provided that substantially no material transfers from the seating surface to the stent. Exemplary tacky seating surfaces include ElastEon™, SIBS, or poly-(ether block amide), (e.g., PEBAX®).

[As yet another example, while certain embodiments have been shown and/or described without a distal tip or a proximal bumper, embodiments generally can have a distal tip (e.g., a bullet-shaped distal tip) and/or a proximal bumper.

Other embodiments are in the claims.

What is claimed is:

1. An implantable medical endoprosthesis delivery system, comprising:
   a delivery catheter;
   a delivery member at least partially disposed within the delivery catheter;
   a first bumper circumferentially disposed around and attached to the delivery member;
   a second bumper circumferentially disposed around and attached to the delivery member; and
   an endoprosthesis circumferentially disposed around the delivery member and longitudinally between the first bumper and the second bumper, wherein the first and second bumpers limit longitudinal movement of the endoprosthesis relative to the delivery member such that, while the endoprosthesis is disposed in the delivery catheter,
      the endoprosthesis remains substantially stationary in a longitudinal direction with respect to the delivery member when the delivery catheter moves proximally or distally with respect to the delivery member, and
      the endoprosthesis remains substantially stationary in a longitudinal direction with respect to the delivery member when the delivery member moves proximally or distally, wherein the first and second bumpers each comprise a helical coil, and
   wherein, while the endoprosthesis is disposed in the delivery catheter, the endoprosthesis is freely rotatable around the delivery member.

2. The system of claim 1, wherein the delivery catheter, the delivery member, the first bumper, the second bumper, and the endoprosthesis are configured to permit rotation of the delivery member while applying substantially no torque to the endoprosthesis.

3. The system of claim 1, wherein the delivery member is formed of a first material, wherein the first and second bumpers are formed of a second material different from the first material.

4. The system of claim 1, wherein the first bumper has a first endoprosthesis-contacting surface disposed on a distally facing end thereof, and wherein the second bumper has a second endoprosthesis-contacting surface disposed on a proximally facing end thereof.

5. The system of claim 1, further comprising a distal end bumper disposed distal of the first and second bumpers.

6. The system of claim 1, further comprising helical windings circumferentially disposed around and attached to the delivery member,
   wherein the helical windings are disposed between the first and second bumpers, and
   wherein an outer diameter of the helical windings is less than an inner diameter of the endoprosthesis when the endoprosthesis is disposed in the delivery catheter.

* * * * *